United States Patent [19]

Ellman et al.

[11] Patent Number: 5,518,310
[45] Date of Patent: May 21, 1996

[54] MOBILE CART FOR ELECTROSURGICAL INSTRUMENT AND ACCESSORIES THEREFOR

[76] Inventors: Alan G. Ellman; Jon C. Garito, both of 1135 Railroad Ave., Hewlett, N.Y. 11557

[21] Appl. No.: 349,427

[22] Filed: Dec. 5, 1994

[51] Int. Cl.⁶ .................................................. A47B 46/00
[52] U.S. Cl. .................. 312/249.12; 312/249.1; 312/223.1; 312/223.6; 312/209
[58] Field of Search ................. 312/249.1, 249.4, 312/249.5, 249.8, 249.11, 249.12, 249.13, 209, 237, 223.6, 400, 223.3, 406, 116, 223.1

[56] References Cited

U.S. PATENT DOCUMENTS

| | | | |
|---|---|---|---|
| 3,715,148 | 2/1973 | Beals | 312/249.11 X |
| 3,997,218 | 12/1976 | Wolf et al. | 312/209 |
| 4,114,965 | 9/1978 | Oye et al. | 312/249.12 X |
| 4,453,694 | 6/1984 | Andreasson | 312/237 X |
| 4,681,378 | 7/1987 | Hellman, III | 312/223.6 X |
| 4,715,512 | 12/1987 | Buchser | 312/406 X |
| 5,016,948 | 5/1991 | Welch et al. | 312/249.12 |
| 5,292,029 | 3/1994 | Pearson | 221/2 |
| 5,306,238 | 4/1994 | Fleenor | 606/42 |
| 5,399,007 | 3/1995 | Marconet | 312/209 |

FOREIGN PATENT DOCUMENTS 3142858  5/1983  Germany ........................... 312/223.6

OTHER PUBLICATIONS

Catalog entitled "Waterloo Storage & Delivery Systems" Sep. 21, 1994.

Primary Examiner—Peter M. Cuomo
Assistant Examiner—James O. Hansen

[57] ABSTRACT

A mobile cart comprises a platform for supporting at least a commercially available electrosurgical instrument or apparatus and a smoke evacuator system. Preferably, the mobile cart contains further means for housing additional accessories. The cart is constructed to provide a protected region within which electrical wiring can be run to ensure the wire does not interfere with the surgeon while performing an electrosurgical procedure.

10 Claims, 4 Drawing Sheets

5,518,310

MOBILE CART FOR ELECTROSURGICAL INSTRUMENT AND ACCESSORIES THEREFOR

This invention relates to a mobile cart for an electrosurgical instrument and accessories therefor.

BACKGROUND OF THE INVENTION

Electrosurgery is becoming a more popular surgical procedure, and as its popularity increases a greater number of accessories are becoming available and are being used by surgeons conducting increasing numbers of medical, dental, and veterinarian procedures. Surgical carts for housing electrosurgical instruments as well as certain accessories are available but most are modifications of surgical carts originally designed for other purposes and are not always the most convenient nor the most functional specifically to assist surgeons conducting electrosurgical procedures. Thus, a need exists in the art for a surgical cart specifically adapted to provide a chairside or table side location not only for an electrosurgical instrument but also for the accessories most frequently used during such procedures.

SUMMARY OF THE INVENTION

An object of the invention is a novel mobile cart providing improved functionality in support of electrosurgical procedures.

According to one aspect of the invention, the mobile cart comprises a platform for supporting at least a commercially available electrosurgical instrument or apparatus, such as the Ellman SURGITRON F.F.P.F. electrosurgical machine, and a smoke evacuator system. Preferably, the mobile cart contains further means for housing additional accessories.

According to another aspect of the invention, the cart is constructed to provide a protected region within which electrical wiring can be run to ensure the wire does not interfere with the surgeon while performing an electrosurgical procedure.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like numerals designating the same or similar parts.

DETAILED DESCRIPTION OF THE PREFERRED EMBODIMENTS

Figure 2:
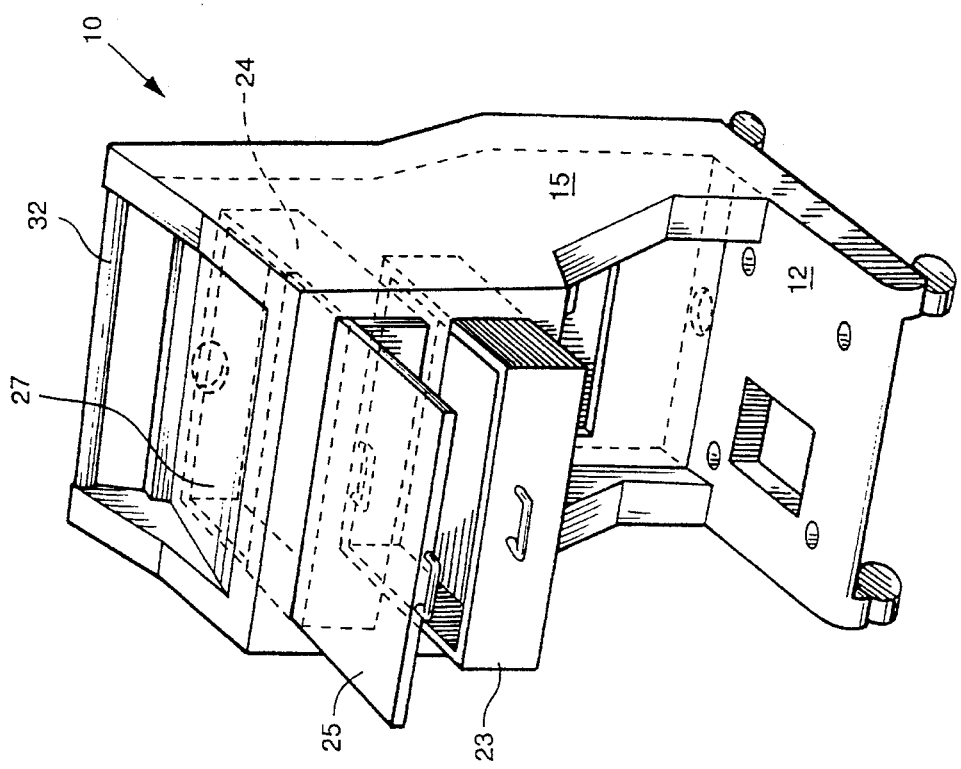
FIG. 2 is a perspective view similar to FIG. 1 showing the cart with extended shelf and drawer.
Figure 1:
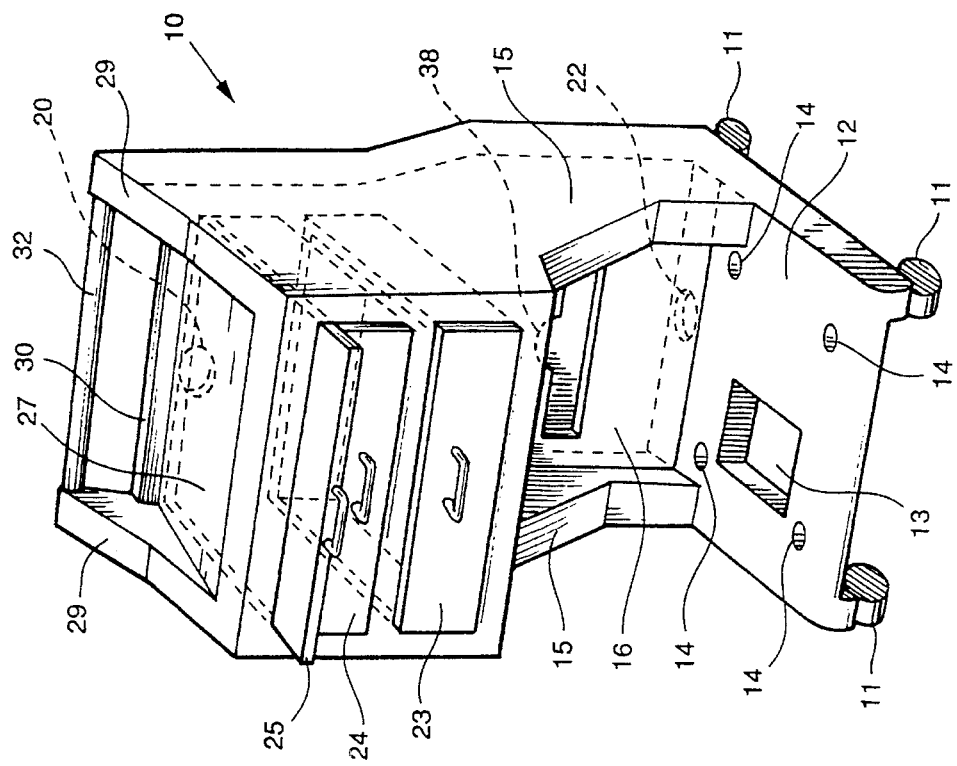
FIG. 1 is a perspective view of one form of mobile cart according to the invention.
Figure 3:
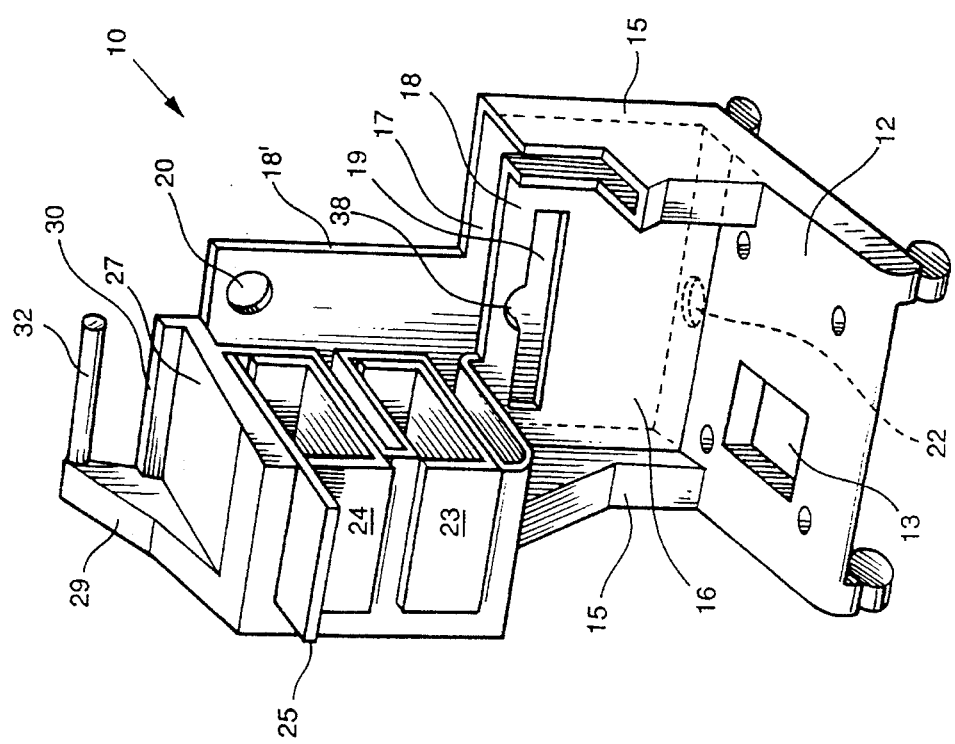
FIG. 3 is a perspective view similar to FIG. 1 with the top quarter cut away to show the interior construction of the cart.

One form of mobile cart according to the invention is illustrated in FIGS. 1–3. The cart 10 comprises a wide stable base 12 mounted on four hospital-grade locking wheels 11. The base 12 contains four holes 14 located at the corners of a rectangle, and a relatively large through-opening 13 inside the rectangle. Upstanding from the base are two side wall sections 15 connected to a rear wall section 16. As will be observed from FIG. 3, the side wall and rear wall sections 15, 16 are double-walled to form a generally empty closed space 17. The front part 18 of the rear wall 16 close to the base contains a first horizontally-elongated opening 19 into the closed space 17, and the rear part 18' of the rear wall 16 contains a second opening 20 higher up also leading from the back into the closed space 17, and the base contains at its bottom an opening 22 leading outwardly to the bottom from the closed space 17. Projecting forward from the rear wall 16 is structure defining two pull-out drawers 23, 24 and a pull-out shelf 25. Above the latter at the top of the cart is a fixed shelf 27 which is slightly tilted downward toward the rear wall. The top shelf 27 is surrounded on three sides by two side walls 29, a rear edge 30, and up above by a horizontal rail 32. FIG. 2 is a similar view showing the bottom drawer 23 extended and the pull-out shelf 25 extended.

Figure 4:
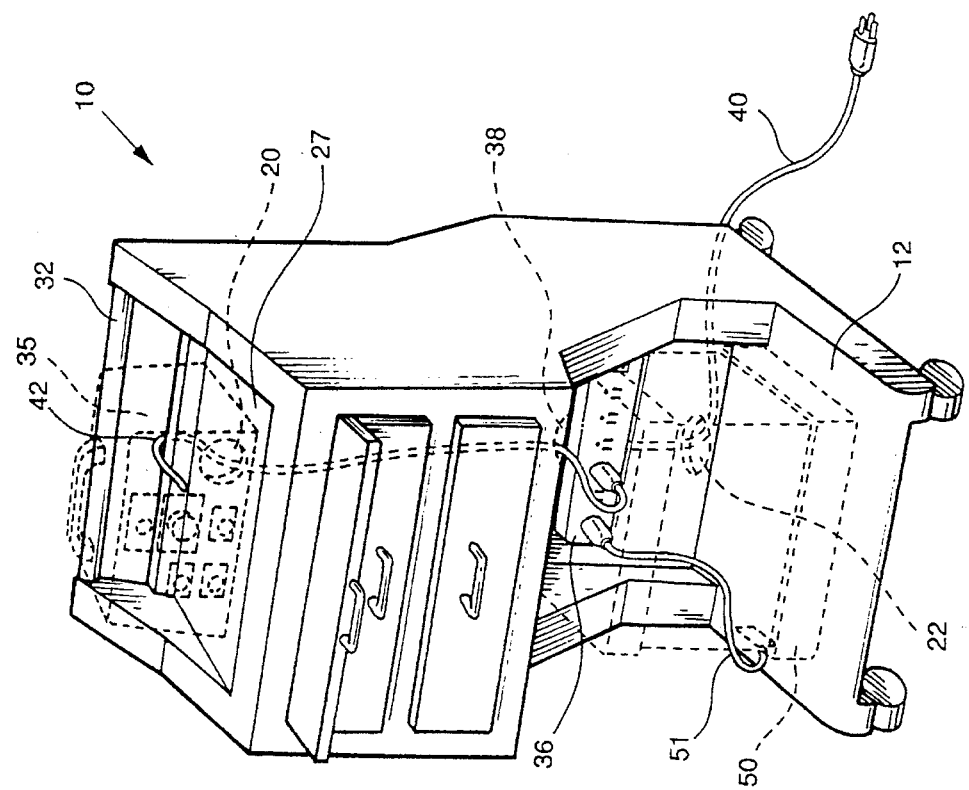
FIG. 4 is a perspective view similar to FIG. 1 showing in phantom an electrosurgical instrument on the cart.

FIG. 4 shows a common way of using the cart 10 of FIG. 1. An electrosurgical instrument 35, in phantom, is shown positioned on the top fixed shelf 27. The tilting of the latter allows easier access to the electrosurgical instrument and improve visibility of its controls. An electrical power strip 36 is mounted in the rectangular opening 19 in the rear wall 10. The power cord 40 of the power strip 36, located at its rear, can now pass through the closed space 17 down to the bottom opening 22 and to the outside for plugging into a local wall socket. The power cord 42 of the electrosurgical instrument 35 can pass through the space under the rail from which it can pass through the opening 20 in the rear wall 16 and into the closed space 17 from which it descends down to a small semi-circular extension 38 of the opening 19 and through the latter where it can be plugged into the power strip 36.

Seated on the bottom shelf 12 is a smoke and odor evacuator machine 50 of a type sold under the tradename Vapor-Vac by the Ellman company. This electrosurgical accessory provides suction at a wand (not shown) attached to the machine and commonly used by surgeons to remove smoke and odors from the surgical site. The power cord 51 for the evacuator machine 50 can be brought through the opening 13 on the bottom shelf 12 and then up and around the side to be plugged into the power strip 30. The four holes 14 in the base 12 are for receiving the feet of the evacuator machine to avoid machine movement when the cart is moved. The drawers can conveniently hold various electrodes, handpieces, and other accessories for use with the electrosurgical instrument. The pull-out shelf 25 provides increased working space if desired. The rail 32 at the top can also serve as a handle for moving the cart.

Preferably, the cart 11 is made of a strong but lightweight plastic so that it is easily managed even with the equipment shown in place.

Figure 5:
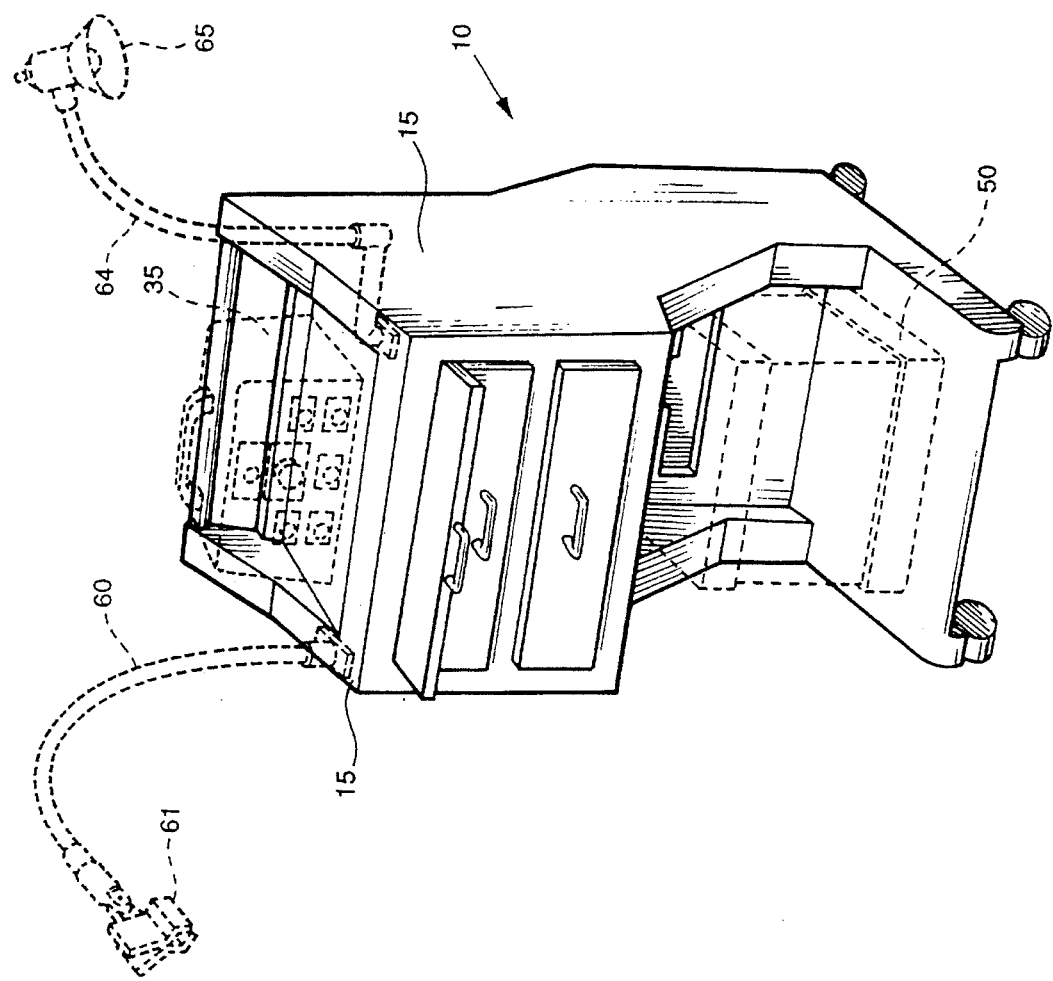
FIG. 5 is a perspective view similar to FIG. 1 showing the cart and in phantom an electrosurgical instrument, an accessory, and a holder and lamp mounted on the cart.
Figure 6:
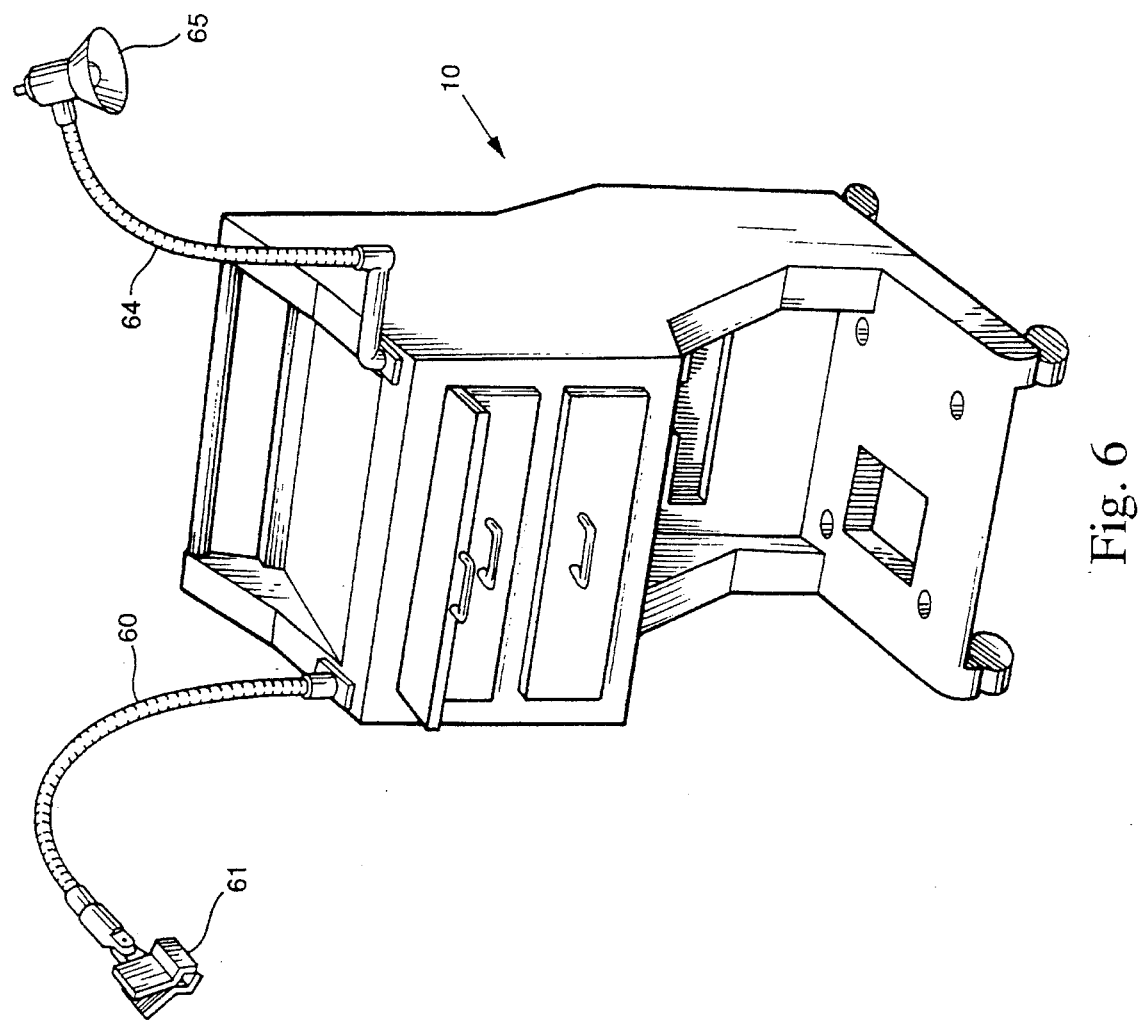
FIG. 6 is a perspective view similar to FIG. 1 of a modification of cart according to the invention.

FIG. 5 is a view similar to FIG. 4 but with two additional accessories permanently mounted on top of the two side walls 15 of the cart 10. The accessory on the left is a gooseneck arm 60 which terminates in an adjustable holder 61 adapted to hold the wand (not shown) used with the evacuator machine and whose end supplies the suction wherever the surgeon needs it. The gooseneck arm 60 allows the surgeon to position the wand wherever desired. The accessory on the right is a similar gooseneck arm 64 but in this case supporting an electric lamp 65 for providing extra illumination of the surgical site. FIG. 6 illustrates a modification in which the cart 10 is provided permanently with the goosenecked holder 60, 61 and goosenecked lamp 64, 65. FIG. 6 also shows a swivel joint 68 at the base of the goosenecked lamp for greater flexibility.

It will be appreciated that the cart of the invention is not limited to use with the Ellman company instrument and accessory but is equally useful to support other brands of electrosurgical instruments and accessories.

The cart of the invention offers the advantages of being uniquely suited for supporting an electrosurgical instrument and accessories therefor at a chairside or tableside location close to where the surgery is to be performed. It provides a central, convenient location for all electrosurgical instruments and accessories. It provides more usable storage space as well as more usable counter space for the surgeon. The inside protected space in which electrical wires can run while yet allowing easy connections both to the instrument or accessory protects against loose external wiring that can interfere with the surgeon. The incorporated power strip provides convenient outlets for plugging in handpieces and bipolar forceps.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed:

1. A mobile cart adapted for supporting an electrosurgical instrument and accessories therefor, comprising:
   (a) a wheeled platform having a base, an upstanding rear wall, and upstanding side walls, said base having a front surface and being sized to receive and support a large accessory for an electrosurgical instrument when placed thereon during use,
   (b) a superstructure supported on the side and rear walls, said superstructure comprising:
      (i) a drawer for holding accessories,
      (ii) a movable shelf above the drawer,
      (iii) a fixed shelf above the movable shelf partly surrounded by side and rear members, said fixed shelf having a front surface and being sized to receive and support an electrosurgical instrument when placed thereon during use,
      (iv) the rear wall comprising double walls providing an empty substantially closed surface for running electrical wiring vertically between the fixed shelf and the base.

2. The mobile cart of claim 1, further comprising a goosenecked holder mounted on top of one of the side walls.

3. The mobile cart of claim 2, further comprising a goosenecked lamp mounted on top of the other of the side walls.

4. The mobile cart of claim 1 in combination with an electrosurgical instrument mounted on the fixed shelf and a smoke evacuator machine mounted on the base.

5. The mobile cart as claimed in claim 1, wherein the fixed shelf is tilted downward toward the rear wall for easier visibility of an instrument when placed on the fixed shelf during use.

6. The mobile cart as claimed in claim 1, wherein the side members surrounding the fixed shelf are lower at the front surface of the fixed shelf for easier access to the fixed shelf.

7. The mobile cart as claimed in claim 1, wherein the upstanding side walls are cut away at the front surface of the base for easier access to the base.

8. The mobile cart as claimed in claim 1, wherein the rear wall has openings to the substantially closed space adjacent the fixed shelf and adjacent the base.

9. A mobile cart adapted for supporting an electrosurgical instrument and accessories therefor, comprising:
   (a) a wheeled platform having a base, an upstanding rear wall, and upstanding side walls, said base being sized to receive and support a large accessory for an electrosurgical instrument when placed thereon during use,
   (b) a superstructure supported on the side and rear walls, said superstructure comprising:
      (i) a drawer for holding accessories,
      (ii) a movable shelf above the drawer,
      (iii) a fixed shelf above the movable shelf partly surrounded by side and rear members, said fixed shelf being sized to receive and support an electrosurgical instrument when placed thereon during use,
   (c) the rear wall being double-walled providing a substantially closed space for running electrical wiring,
   (d) a front part of the double-walled rear wall having an elongated first opening for receiving an electrical power strip, a rear part of the double-walled rear wall having a second opening for receiving an electrical power cord, and the base below the closed space having an opening for passing electrical cords.

10. The mobile cart of claim 9, wherein the first opening has an extended opening for passing an electrical cord.

* * * * *